(12) United States Patent
Kataoka et al.

(10) Patent No.: US 7,450,685 B2
(45) Date of Patent: Nov. 11, 2008

(54) X-RAY FLUORESCENCE SPECTROMETER AND PROGRAM FOR USE THEREWITH

(75) Inventors: Yoshiyuki Kataoka, Takatsuki (JP); Hisayuki Kohno, Takatsuki (JP); Masatsugu Kuraoka, Takatsuki (JP); Takashi Shoji, Takatsuki (JP); Yasujiro Yamada, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 65 days.

(21) Appl. No.: 11/581,487

(22) Filed: Oct. 17, 2006

(65) Prior Publication Data

US 2007/0086567 A1    Apr. 19, 2007

(30) Foreign Application Priority Data

Oct. 19, 2005 (JP) ............................. 2005-304664
Sep. 6, 2006 (JP) ............................. 2006-241760

(51) Int. Cl.
*G01N 23/223* (2006.01)
(52) U.S. Cl. ......................................... 378/45; 378/50
(58) Field of Classification Search ................... 378/44, 378/45, 50
See application file for complete search history.

(56) References Cited

U.S. PATENT DOCUMENTS 5,067,111 A * 11/1991 Asano et al. ........... 365/189.08

OTHER PUBLICATIONS

Chemical State Analysis of Sulfur, Chromium and Tin by High Resolution x-Ray Spectrometry; Gohshi, et al., Advances in X-ray Analysis, vol. 18, 1975, pp. 406-414.
Limit I in chemical Condition Analyzing Method Using Two Crystal-Type High Resolution Fluorescent X-ray Technology; Asahi Kasei Analysis & Simulation; May 24, 2003.

* cited by examiner

*Primary Examiner*—Chih-Cheng G Kao
(74) *Attorney, Agent, or Firm*—Sughrue Mion, PLLC (57) ABSTRACT

A scanning X-ray fluorescence spectrometer includes a quantitatively analyzing device (18) which calculates the concentration of hexavalent chrome based on the fact that the peak spectroscopic angle, at which the maximum intensity is attained in Cr—K$\alpha$ line (22), changes depending on the ratio of the concentration of the hexavalent chrome vs. the concentration of the intensity of the total chrome. A plurality of detecting device (23) having different resolutions as a combination of a divergence slit (11), a spectroscopic device (6), a receiving slit (20) and a detector (8) is provided such that when the change of the peak spectroscopic angle is to be detected, a detecting device (23B) having a higher resolution than that of the detecting device (23A), which is selected when the concentration or the intensity of the total chrome is to be determined, is selected.

8 Claims, 5 Drawing Sheets

X-RAY FLUORESCENCE SPECTROMETER AND PROGRAM FOR USE THEREWITH

BACKGROUND OF THE INVENTION 1. (Field of the Invention)

The present invention relates to an X-ray fluorescence spectrometer for quantitatively analyzing hexavalent chromium and a program for use therewith.

2. (Description of the Prior Art)

It is well known that chromium exist in various forms such as, for example, metal chrome (zero-valent chrome), trivalent chrome and hexavalent chrome and, of those chromes, the hexavalent chrome has such a high toxicity that quantitative analysis thereof is often required separately from the other chromes.

For the quantitative analysis of the hexavalent chrome through the X-ray fluorescence analysis, a method is known, in which using an X-ray fluorescence spectrometer of a type capable of continuously monochromating (in two stages) fluorescent X-rays, emitted from a sample, by means of two spectroscopic devices, i.e., a so-called double crystal spectrometer, Cr—K$\beta$1 line is measured to thereby quantitatively analyze trivalent chrome and hexavalent chrome separately. See, for example, Y. Gohshi et al, "Advances in X-ray Analysis" (USA) 1975, Vol. 18, p. 406-414.

It is also known that using the double crystal spectrometer, Cr—K$\alpha$ line is measured so that trivalent chrome and hexavalent chrome can be identified in reference to the shift of a peak and the FWHM (full width at half maximum) of the peak and the trivalent chrome and metal chrome can be identified in reference to the FWHM of the peak. See, for example, "Nikesshogata Koubunnkainou Keikou X-senn-hou niyoru Kagakujoutai-bunnsekihou no Hantei-genkai I (Limit I in Chemical State Analyzing Method Using Double Crystal-type High Resolution Fluorescent X-ray Technology) published May 24, 2003 at the 64-th Discussion on Analytic Chemistry.

However, in any of those known method, the use of the double crystal spectrometer is essential, which is a complicated and bulky X-ray fluorescence spectrometer. In particular, the first described prior art method is silent as to whether or not the metal chrome and the hexavalent chrome can be quantitatively analyzed separately and, on the other hand, the second described prior art method is specifically intended to determine the valence of the chrome and not to quantitatively analyze the chromes separately according to the valence and is therefore unable to quantitatively analyze the hexavalent chrome separately from any other chromes. Also, other known analytical technologies than the X-ray fluorescence analysis are based on a destructive test and/or require complicated and time-consuming analytical procedures.

SUMMARY OF THE INVENTION

In view of the above, the present invention is intended to provide an X-ray fluorescence spectrometer of a simplified construction capable of accomplishing a quantitative analysis of the hexavalent chrome.

It is an important object of the present invention to provide a program that can be used in the practice of the fluorescence X-ray analysis in accordance with the present invention.

In order to accomplish these objects, the present invention provides an X-ray fluorescence spectrometer which includes an X-ray source for irradiating a sample with primary X-rays; a divergence slit for passing therethrough fluorescent X-rays generated from the sample; a spectroscopic device for monochromating the fluorescent X-rays having passed through the divergence slit; a receiving slit for passing therethrough the fluorescent X-rays having been monochromated by the spectroscopic device; a detector for detecting an intensity of the fluorescent X-rays; a interlocking drive device for driving the spectroscopic device, the receiving slit and the detector in association with each other so that while the wavelength of the fluorescent X-rays monochromated at a spectroscopic angle of the spectroscopic device that is changed is varied, the fluorescent X-rays so monochromated can impinge on the receiving slit and the detector; and a quantitatively analyzing device for performing the quantitative analysis based on a result of measurement by the detector.

The quantitatively analyzing device referred to above is operable to calculate the concentration or the amount of deposit of hexavalent chrome based on the fact that the spectroscopic angle of the peak, at which the maximum intensity is attained in Cr—K$\alpha$ line, changes depending on the ratio of the concentration or the intensity of the hexavalent chrome vs. the concentration of the intensity of the total chrome. Also, at least one of the divergence slit, the spectroscopic device and the receiving slit is provided selectively in a plural number so as to form a plurality of detecting device having different resolutions from each other as a combination of the divergence slit, the spectroscopic device, the receiving slit and the detector, such that when the change of the peak spectroscopic angle is to be detected, a detecting device having a higher resolution than that of the detecting device, which is selected when the concentration or the intensity of the total chrome is to be determined, is selected.

The X-ray fluorescence spectrometer of the structure designed according to the foregoing aspect of the present invention is an X-ray fluorescence spectrometer of a type, in which the fluorescent X-rays from the sample are monochromated by the only one spectroscopic device employed or a selected one from spectroscopic devices, that is, a so-called single crystal spectrometer. In this spectrometer, the quantitatively analyzing device calculates the concentration or the amount of deposit of the hexavalent chrome based on the fact that the peak spectroscopic angle, at which the maximum intensity is attained in Cr—K$\alpha$ line, varies depending on the ratio of the concentration or the intensity of the hexavalent chrome vs. the concentration or the intensity of the total chrome and, accordingly, the hexavalent chrome can be quantitatively analyzed with a simplified structure. This is possible because when the change of the peak spectroscopic angle is to be detected, the high resolution detecting device having a resolution higher than that of the detecting device, which is selected when the concentration or the intensity of the total chrome is to be determined, is selected.

In the X-ray fluorescence spectrometer of the structure described above, it is preferred that the quantitatively analyzing device stores therein a correlation between a ratio of the intensity at a predetermined spectroscopic angle on a smaller angle side than the peak in Cr—K$\alpha$ line vs. the intensity at a predetermined spectroscopic angle on a larger angle side than the peak and a ratio of the concentration of the hexavalent chrome vs. the concentration of the total chrome, which have been determined using standard samples, and calculates the concentration of the hexavalent chrome in a sample to be analyzed, by determining, with respect to a sample to be analyzed, the ratio of the intensities, applying it to the correlation and applying the concentration of the total chrome so determined to the ratio of the concentrations so obtained. In this case, the receiving slit is preferably provided selectively in a plural number such that when the ratios of the intensities are to be determined, a receiving slit having a higher resolution than that of a receiving slit, which is selected when the concentrations of the total chrome are determined, is selected. According to this preferred structural feature, based on the conventional scanning type X-ray fluorescence spectrometer, the X-ray fluorescence spectrometer according to the above mentioned aspect of the present invention can easily be realized.

Also, in the X-ray fluorescence spectrometer according to the foregoing aspect of the present invention, where the sample includes a chromate treatment film and a substrate in the form of a sheet steel or galvanized sheet steel positioned beneath the chromate treatment film, the quantitatively analyzing device employed therein is so designed and so configured as to store therein a correlation between a ratio of the intensity at a predetermined spectroscopic angle on a smaller angle side than the peak in Cr—Kα line vs. the intensity at a predetermined spectroscopic angle on a larger angle side than the peak, that is, a first intensity ratio, and a ratio of the intensity from the hexavalent chrome vs. the intensity from the total chrome, that is, a second intensity ratio, which have been determined using a standard sample, and also to store therein an analytical curve descriptive of the relationship between the intensity from the total chrome and the amount of deposit of chrome contained in the chromate treatment film, and to calculate the amount of deposit of the hexavalent chrome in the chromate treatment film by, with respect to the sample to be analyzed, determining and applying the first intensity ratio to the correlation, applying the intensity from the total chrome, so determined, to the second intensity ratio to thereby calculate the intensity from the hexavalent chrome and multiplying the intensity from the hexavalent chrome by a gradient of the analytical curve.

And, the receiving slit is preferably provided selectively in a plural number such that when the first intensity ratios are to be determined, a receiving slit having a higher resolution than that of a receiving slit, which is selected when the intensities from the total chrome are determined, is selected. According to this preferred structural feature, not only can the X-ray fluorescence spectrometer be easily realized based on the conventional scanning type X-ray fluorescence spectrometer, but any influence brought about by chrome contained in the substrate, i.e., the galvanized sheet steel or the sheet steel can be excluded.

In any one of the preferred structural features described above, in place of the intensity at each of the predetermined spectroscopic angles with respect to the standard sample and the sample to be analyzed, a ratio between the intensity thereof and the intensity at each of the predetermined spectroscopic angles with respect to a monitor sample may be utilized. Although it may occur that the predetermined spectroscopic angles may displace as a result of the use of the spectrometer for a long period of time and/or a change in temperature inside the spectrometer, this permits any influence, resulting from displacement of the predetermined spectroscopic angles, to be corrected.

Also, in any one of the preferred structural features described above, it is preferable that Cr—Kα1 line is measured using pure metal chrome and trivalent chrome as samples; peak profiles normalized with their integrated intensities are determined; spectroscopic angles, at which respective intensities of the peak profiles forwardly and rearwardly of a peak spectroscopic angle of Cr—Kα1 line match with each other, is determined; and the quantitatively analyzing device stores therein the two spectroscopic angles, so determined, as the predetermined spectroscopic angle on the smaller angle side and the predetermined spectroscopic angle on the larger angle side, respectively. Although the respective peak profiles of the metal chrome and the trivalent chrome differ slightly from each other, measurement with the predetermined spectroscopic angles so determined in the manner described above is effective to render the ratio of the intensity at the predetermined spectroscopic angle on the smaller angle side vs. the intensity at the predetermined spectroscopic angle on the larger angle side of the metal chrome and the trivalent chrome to match with each other, thereby excluding any influence brought about by the difference in those peak profiles and, accordingly the hexavalent chrome can further accurately be analyzed quantitatively.

Furthermore, in the X-ray fluorescence spectrometer of the structure according to the foregoing aspect of the present invention, the quantitatively analyzing device may be so designed and so configured as to perform, when the concentration or the intensity of the total chrome is to be determined, a qualitative analysis based on a result of measurement done by the detector, to perform a quantitative analysis based on a result of the qualitative analysis and to render the value of chrome analyzed, appearing in a result of the quantitative analysis, to be the concentration or the intensity of the total chrome, that is, so-called semi quantitative analysis.

The present invention in accordance with another aspect thereof provides a program required for causing a computer to function as a quantitatively analyzing device employed in the X-ray fluorescence spectrometer of the structure according to the foregoing aspect of the present invention. Even with this program, functions and effects similar to those exhibited by the X-ray fluorescence spectrometer according to the foregoing aspect can be obtained.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF THE PREFERED EMBODIMENTS

Figure 1:
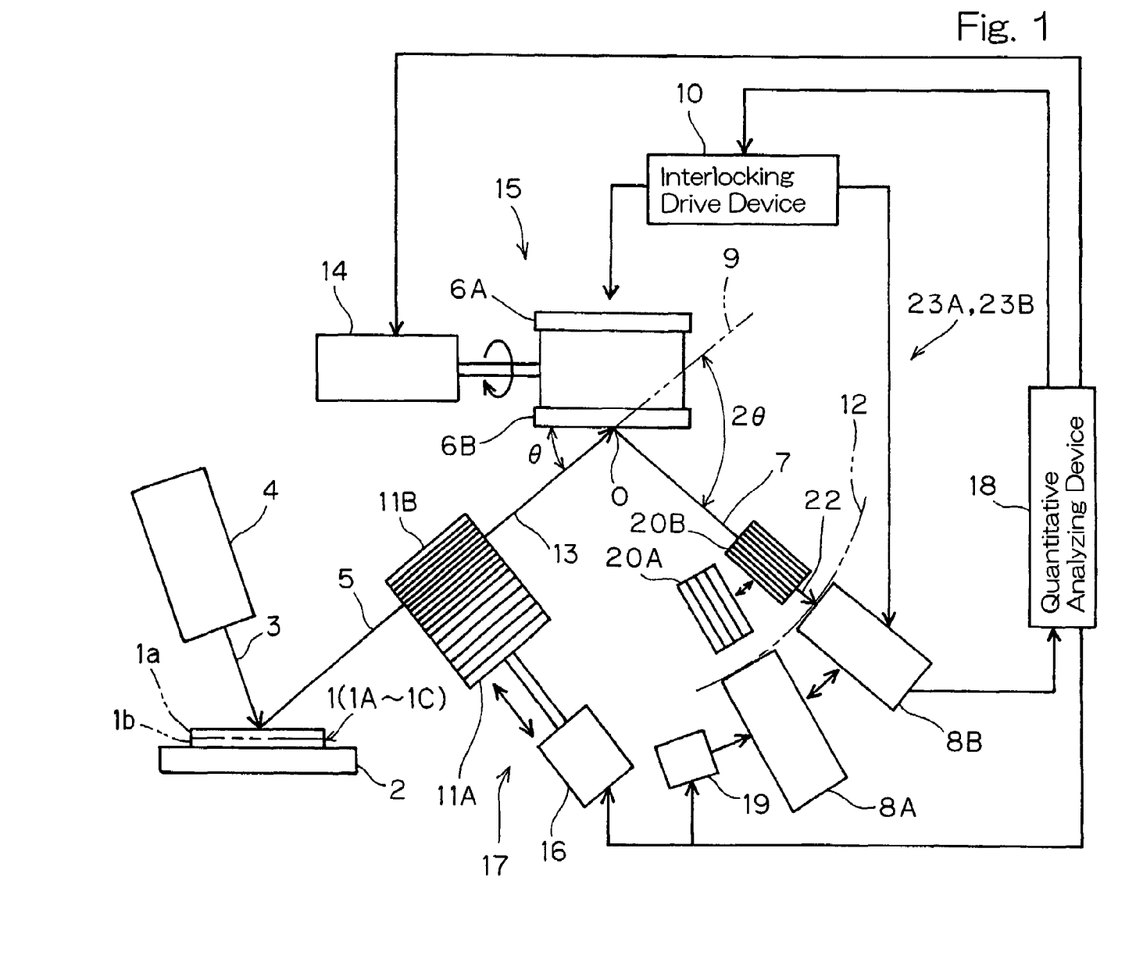
FIG. 1 is a schematic diagram showing an X-ray fluorescence spectrometer according to a preferred embodiment of the present invention.

An X-ray fluorescence spectrometer according to a preferred embodiment of the present invention will now be described in detail with reference to the accompanying drawings. Particularly as shown in FIG. 1, the X-ray fluorescence spectrometer of the present invention is an X-ray fluorescence spectrometer of a wavelength dispersive and scanning type including an X-ray source 4 such as, for example, an X-ray tube for emitting primary X-rays 3 so as to impinge on a sample 1 placed on a sample table 2; a divergence slit 11 for passing therethrough fluorescent X-rays 5 emitted from the sample 1; a spectroscopic device 6 for monochromating the fluorescent X-rays 13 having passed through the divergence slit 11; a receiving slit 20 for passing therethrough the fluorescent X-rays 7 having been monochromated by the spectroscopic device 6; a detector 8 for measuring the intensity of the fluorescent X-rays 22 having passed through the receiving slit 20; a interlocking drive device for driving the spectroscopic device 6, the receiving slit 20 and the detector 8 in association with each other so that while the wavelength of the fluorescent X-rays 7 monochromated at a spectroscopic angle 2θ of the spectroscopic device 6 that is changed is varied, the fluorescent X-rays 7 so monochromated can impinge on the receiving slit 20 and the detector 8; and a quantitatively analyzing device 18 for performing the quantitative analysis based on a result of measurement by the detector 8.

In this X-ray fluorescence spectrometer of the structure described above, each of the divergence slit 11, the spectroscopic device 6 and the receiving slit 20 is provided selectively in a plural number so as to form a plurality of detecting device 23 having different resolutions (angle resolutions) from each other as a combination of the divergence slit 11, the spectroscopic device 6, the receiving slit 20 and the detector 8.

More specifically, the illustrated X-ray fluorescence spectrometer is provided with a plurality of kinds of divergence slits 11 capable of confronting the sample 1 at a predetermined angle of detection and passing therethrough the fluorescent X-rays 5 emitted from the sample 1 and also with a divergence slit exchanger 17 for exchanging one divergence slit 11 with another one of the other divergence slits by means of a plunger 16 or the like. The plural divergence slits 11 are Soller slits having different opening angles from each other and, in the instance as shown, only a standard divergence slit 11A and a high resolution divergence slit 11B are shown.

Also, the illustrated X-ray fluorescence spectrometer is provided with a plurality of kinds of spectroscopic devices 6 and also with a spectroscopic device exchanger 16 for selectively advancing one of the spectroscopic devices 6 into an optical path, along which the fluorescent X-rays 13 having passed through the divergence slit 11 travel, to thereby monochromate the incident fluorescent X-rays 13. The spectroscopic device exchanger 15 is of a type including a drive motor 14 having a rotary shaft on which a polygonal pole coaxially mounted thereon for rotation together therewith, in which the different kinds of spectroscopic devices 6 are fitted to respective side faces of the polygonal pole. In the instance as shown, only a standard spectroscopic device 6A, which is Li F(200), and a high resolution spectroscopic device 6B, which is Li F(220), are shown. One of the spectroscopic device selected upon rotation of the drive motor 14 monochromates the fluorescent X-rays 13 having passed through the divergence slit 11.

Similarly, the illustrated X-ray fluorescence spectrometer is provided with a plurality of receiving slits 20. In the instance as shown, only a standard receiving slit 20A and a high resolution receiving slit 20B, two Soller slits having different opening angles from each other, are shown. Also, the detector 8 is similarly provided in a plural number. In the instance as shown, only a detector 8A, which is F-PC (a gas flow type proportional counter), and a detector 8B, which is SC (a scintillation counter) are shown. It is to be noted that with respect to the detector 8, there is no dominance in angular resolution. In the instance as shown, the standard receiving slit 20A is fixed in front of the detector 8A, which is F-PC, and the high resolution receiving slit 20B is fixed in front of the detector 8B, which is SC. The X-ray fluorescence spectrometer is equipped with a detector changer 19 for selectively advancing one of the detectors 8 into an optical path, along which the fluorescent X-rays 7 having been monochromated by the spectroscopic device 6 travel. Since a combination of the receiving slit 20 and the detector 8 is fixed, the detector changer 19 is operable to selectively advance one of the receiving slits 20 into the optical path of travel of the fluorescent X-rays 7 having been monochromated by the spectroscopic device 6.

As described above, by providing each of the divergence slit 11, the spectroscopic device 6 and the receiving slit 20 selectively in a plural number, a plurality of detecting device having different resolutions from each other as a combination of the divergence slit 11, the spectroscopic device 6, the receiving slit 20 and the detector 8, for example, a standard detecting device 23A, which is a combination of the divergence slit 1B, the spectroscopic device 6B, the receiving slit 20A and the detector 8A, and a high resolution detecting device 23B, which is a combination of the divergence slit 11B, the spectroscopic device 6B, the receiving slit 20B and the detector 8B, can be constructed.

The interlocking drive device 10 referred to above is a so-called goniometer. When the fluorescent X-rays 13 impinges on the selected spectroscopic device 6B at a certain incident angle θ, an extension line 9 of the fluorescent X-rays 13 and the fluorescent X-rays 7 monochromated (diffracted) by the spectroscopic device 6B forms a spectroscopic angle 2θ, which is twice the incident angle θ. The interlocking drive device 10 rotates the spectroscopic device 6B through the spectroscopic device changer 15 about an axis O passing through the geometric center of a surface of the spectroscopic device 6B and perpendicular to the plane of the sheet of the figure and also rotates (scans) the receiving slit 20B and the detector 8B about the axis O along a circle 12 over an angle, which is twice the angle of rotation of the spectroscopic device 6B, so that while the wavelength of the fluorescent X-rays 7, that is monochromated at a spectroscopic angle 2θ that is changed, is varied, the fluorescent X-rays 7 so monochromated can impinge on the selected receiving slit 20B and the selected detector 8B.

The quantitatively analyzing device 18 is operable to calculate the concentration or the amount of deposit of the hexavalent chrome based on the fact that the spectroscopic angle of the peak, at which the maximum intensity is attained in Cr—Kα line 22, changes depending on the ratio of the concentration or the intensity of the hexavalent chrome vs. the concentration or the intensity of the total chrome. When the change of the peak spectroscopic angle is to be detected, the high resolution detecting device 23B having a higher resolution than that of the standard detecting device 23A, which is selected when the concentration of or the intensity of the total chrome is to be determined, is selected.

More specifically, the quantitatively analyzing device 18 is in the form of a computer and stores therein a correlation between a ratio of the intensity at a predetermined spectroscopic angle on a smaller angle side than the peak in Cr—Kα line 22 vs. the intensity at a predetermined spectroscopic angle on a larger angle side than the peak and a ratio of the concentration of the hexavalent chrome vs. the concentration of the total chrome, which have been determined using a standard sample 1A, and calculates the concentration of the hexavalent chrome in a sample 1B to be analyzed, by determining, with respect to a sample 1B to be analyzed, the ratio of the intensities, applying it to the correlation and applying the concentration of the total chrome so determined to the ratio of the concentrations so obtained. With respect to the selection of the detecting device 23 by the quantitatively analyzing device 18, the receiving slit 20B having a higher resolution than that of the receiving slit 20A, which is selected when the concentrations of the total chrome are to be determined, is selected when the ratios of the previously described intensities are to be determined.

The operation of the X-ray fluorescence spectrometer of the structure described above will now be described. At the outset, with respect to a standard sample 1A, which is, for example, 100% metal chrome, and a standard sample 1A, which is 100% trivalent chrome ($Cr_2O_3$), Cr—Kα line 22 are measured with the use of the high resolution detecting device 23B to determine peak profiles that are normalized with their integrated intensities, followed by determination of the spectroscopic angle, at which the respective intensities of the peak profiles match with each other on respective sides of the peak spectroscopic angle of Cr—Kα line 22. The two spectroscopic angles so determined are stored in the quantitatively analyzing device 18 as the predetermined spectroscopic angle $2\theta_L$ on the smaller angle side and the predetermined spectroscopic angle $2\theta_H$ on the larger angle side, respectively.

Then, with respect to a plurality of standard samples 1A of different known compositions but all containing chrome, and with the use of the high resolution detecting device 23B, the intensity $I_L$ at the predetermined spectroscopic angle $2\theta_L$ on the smaller angle side and the intensity $I_H$ at the predetermined spectroscopic angle $2\theta_H$ on the larger angle side are measured to determine the correlation between the ratio $I_H/I_L$ of those intensities and the ratio $W_{6+}/W_{TL}$ of the concentration $W_{6+}$ of the hexavalent chrome vs. the concentration $W_{TL}$ of the total chrome, followed by storage thereof. The inventors of the present invention have found that the linear correlation such as shown by the solid line in FIG. 2 could be obtained.

Figure 4:
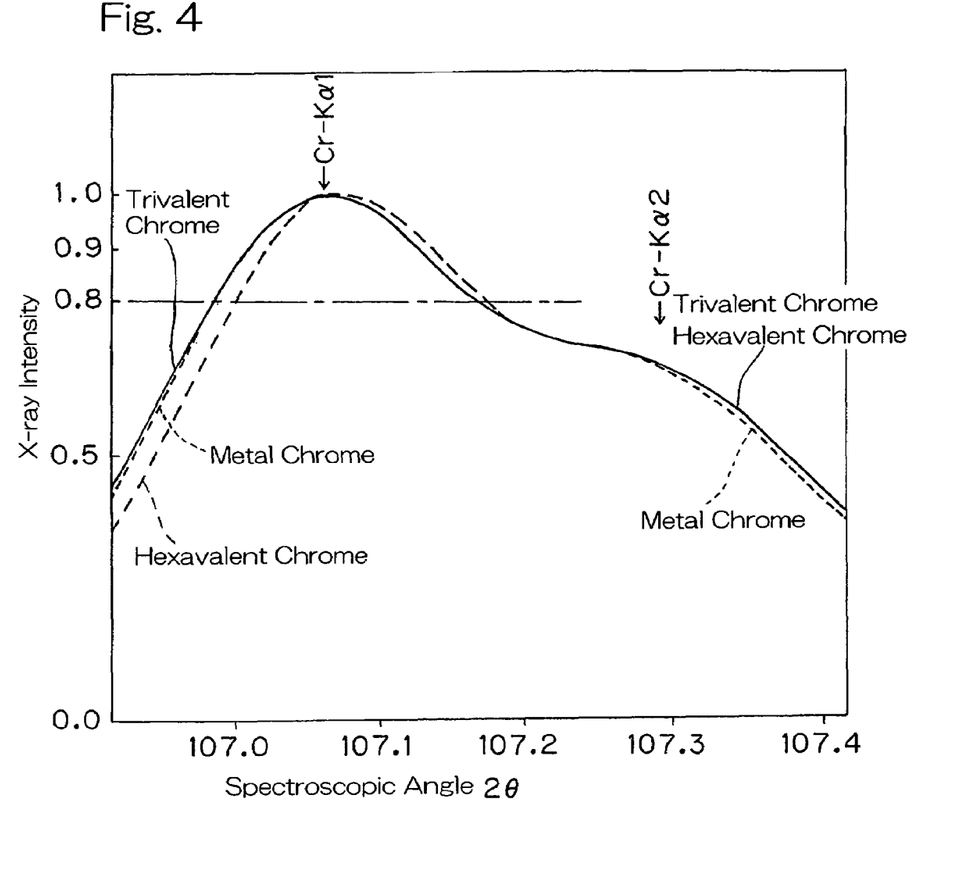
FIG. 4 is a chart showing a peak profile of Cr—Kα line emitted from each of metal chrome, trivalent chrome and hexavalent chrome, which is measured with the X-ray fluorescence spectrometer shown in FIG. 1.

The reason that such correlation can be obtained may be considered as follows. In FIG. 1, using pure metal chrome, trivalent chrome and hexavalent chrome as respective samples 1, the peak profiles measured of Cr—Kα lines 22 are shown in FIG. 4. The peak profiles each normalized with their integrated intensities are shown in overlapped relation. According to this, it can readily be understood that with respect to the peaks of Cr—Kα1 line, when the relative intensity is of a value equal to or higher than about 0.8, the peak of the metal chrome and the peak of the trivalent chrome match with each other (substantially overlap with each other), but differ from (do not overlap with) the peak of the hexavalent chrome. Accordingly, with respect to the peak profiles of the metal chrome and trivalent chrome, the spectroscopic angle at which the respective intensities of the peak profiles on respective sides of the peak spectroscopic angle of Cr—Kα1 line match with each other (the difference in intensity becomes zero), and the two spectroscopic angles thereof are rendered to be the predetermined spectroscopic angle $2\theta_L$ on the smaller angle side and the predetermined spectroscopic angle $2\theta_H$ on the larger angle side, respectively.

Figure 2:
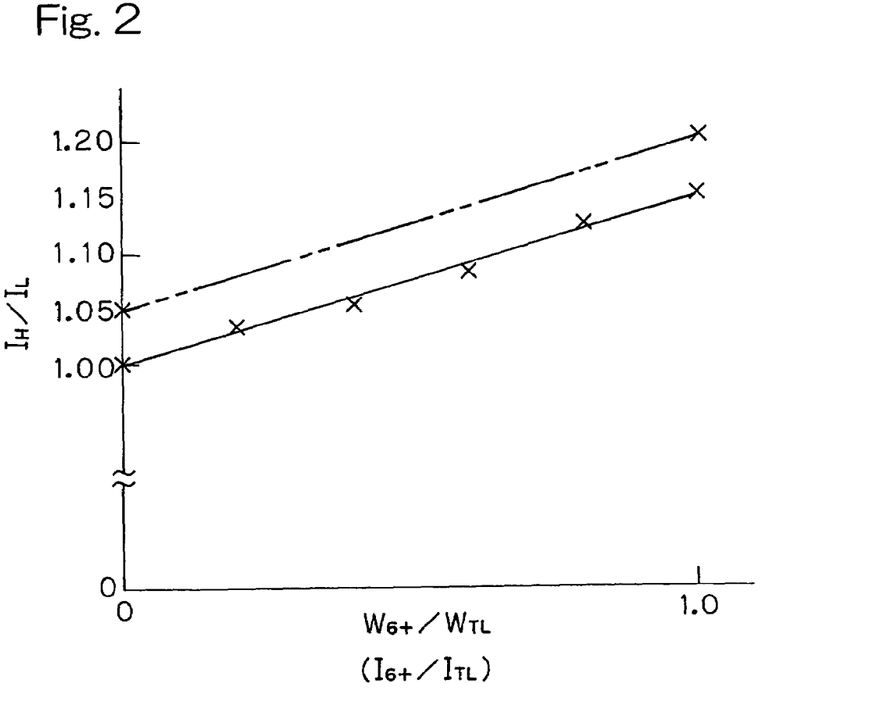
FIG. 2 is a chart showing a correlation that can be used in the X-ray fluorescence spectrometer for calculating the concentration of or the amount of deposit of a hexavalent chrome.

While the peak profile of the metal chrome and that of the trivalent chrome differ slightly from each other, measurement of the sample 1 containing chrome while the predetermined spectroscopic angles $2\theta_L$ and $2\theta_H$ are determined in the manner described above can reveal that irrespective of the ratio between the respective concentrations of the metal chrome and the trivalent chrome, the ratio of the intensity at the predetermined spectroscopic angle $2\theta_L$ on the smaller angle side vs. the intensity at the predetermined spectroscopic angle $2\theta_H$ on the larger angle side becomes equal between the metal chrome and the trivalent chrome, thus eliminating influences brought about by the difference in peak profiles therebetween and, hence, the metal chrome and the trivalent chrome can be regarded as identical with each other and can therefore be distinguish from the hexavalent chrome. Accordingly, such a correlation as shown in FIG. 2 can be obtained.

Thereafter, by means of the quantitatively analyzing device 18, with respect to the sample 1B to be analyzed, using the high resolution detecting device 23B the intensity $I_L$ at the predetermined spectroscopic angle $2\theta_L$ on the smaller angle side and the intensity $I_H$ at the predetermined spectroscopic angle $2\theta_H$ on the larger angle side are measured to determine the ratio $I_H/I_L$ of the measured intensities, which is applied to the correlation referred to above to obtain the ratio $W_{6+}/W_{TL}$ of the concentrations. Also, with respect to the sample 1B to be analyzed, using the standard detecting device 23A the intensity $I_{TL}$ of the total chrome at the peak spectroscopic angle is measured to determine the concentration $W_{TL}$ of the total chrome by means of the conventional analytical curve method. The concentration $W_{TL}$ of the total chrome so determined is applied to the ratio $W_{6+}/W_{TL}$ of the concentrations so obtained to calculate the concentration $W_{6+}$ of the hexavalent chrome. In other words, by means of the quantitatively analyzing device 18, the concentration $W_{6+}$ of the hexavalent chrome is automatically calculated with respect to the sample 1B to be analyzed.

The X-ray fluorescence spectrometer according to the foregoing embodiment is an X-ray fluorescence spectrometer of a type, in which the fluorescent X-rays 5 from the sample 1 are monochromated only at one time by the only selected spectroscopic device 6, that is, a so-called single crystal spectrometer. In this spectrometer, the quantitatively analyzing device 18 calculates the concentration $W_{6+}$ of the hexavalent chrome based on the fact that the peak spectroscopic angle, at which the maximum intensity is attained in Cr—Kα line 22, varies depending on the ratio $W_{6+}/W_{TL}$ of the concentration of the hexavalent chrome vs. the concentration of the total chrome and, accordingly, the hexavalent chrome can be quantitatively analyzed with a simplified structure. In particular, the X-ray fluorescence spectrometer according to the foregoing embodiment can be constructed simply by modifying contents of operation of the quantitatively analyzing device 18 based on the conventional scanning type X-ray fluorescence spectrometer. The reason that with such a simple structure the hexavalent chrome can be quantitatively analyzed is because when change of the peak spectroscopic angle is to be detected, that is, when the intensity ratios $I_H/I_L$ discussed above are to be determined, the detecting device 23B having a higher resolution than that of the detecting device 23A that is selected when the concentrations $W_{TL}$ of the total chrome are to be determined is selected.

Also, the quantitatively analyzing device 18 used in this X-ray fluorescence spectrometer can be so designed and so configured as to operate in the following manner so that it can be used with the sample 1 of a kind including a chromate treatment film 1a (containing hexavalent chrome and trivalent chrome) and a substrate 1b in the form of a sheet steel or a galvanized sheet steel (both containing metal chrome). At the outset, using a standard sample 11A, the correlation between the ratio of the intensity $I_L$ at a predetermined spectroscopic angle $2\theta_L$ on the smaller angle side of the peak in Cr—Kα line 22 vs. the intensity $I_H$ at the predetermined spectroscopic angle $2\theta_H$ on the larger angle side of the peak, that is, a first intensity ratio $I_H/I_L$, and the ratio of the intensity $I_{6+}$ from the hexavalent chrome vs. the intensity $I_{TL}$ from the total chrome, that is, a second intensity ratio $I_{6+}/I_{TL}$ (The details of how to determine it will be described later.) is stored beforehand and the analytical curve descriptive of the relationship between the intensity $I_{TL}$ from the total chrome and the amount of deposit $C_{FTL}$ of chrome contained in the chromate treatment film, which have been determined using the standard sample 1A, are stored.

Then, with respect to a sample 1B to be analyzed, the first intensity ratio $I_H/I_L$ is determined and applied to the previously described correlation, the intensity $I_{TL}$ from the total chrome so determined is applied to the second intensity ratio $I_{6+}/I_{TL}$ obtained to calculate the intensity $I_{6+}$ from the hexavalent chrome, followed by multiplication of the intensity $I_{6+}$ of the hexavalent chrome by a gradient of the analytical curve referred to above to thereby calculate the amount of deposit $C_{6+}$ of the hexavalent chrome contained in the chromate treatment film. Also, in determination of the intensity ratios $I_H/I_L$ referred to above, the detecting device 23B (including the high resolution receiving slit 20B) having a resolution higher than that of the detecting device 23A (including the standard receiving slit 20A), which is used during the determination of the intensities $I_{TL}$ from the total chrome, is selected.

The operation of the X-ray fluorescence spectrometer, which applies where the sample 1 is made up of the chromate treatment film 1a and the substrate in the form of the galvanized sheet steel 1b, will now be described. In the first place, in a manner similar to that described previously, the predetermined spectroscopic angle $2\theta_L$ on the smaller angle side and the predetermined spectroscopic angle $2\theta_H$ on the larger angle side are stored in the quantitatively analyzing device 18.

Then, with respect to the plural standard samples 1A having different but known amounts of deposit of chrome for each valence in the chromate treatment films 1a and also having known concentrations of metal chrome in the galvanized sheet steels 1b, using the high resolution detecting device 23B, the intensity $I_L$ at the predetermined spectroscopic angle $2\theta_L$ on the smaller angle side and the intensity $I_H$ at the predetermined spectroscopic angle $2\theta_H$ on the larger angle side are measured and the correlation between the intensity ratio thereof, that is, a first intensity ratio $I_H/I_L$, and the ratio of the intensity $I_{6+}$ from the hexavalent chrome vs. the intensity $I_{TL}$ from the total chrome, that is, a second intensity ratio $I_{6+}/I_{TL}$ is determined and is then stored. Although in determination of the second intensity ratio $I_{6+}/I_{TL}$, the amount of deposit $C_{6+}$ of the hexavalent chrome and the amount of deposit $C_{TL}$ of the total chrome (including a contribution of the metal chrome contained in the galvanized sheet steel 1b) are required to be converted into respective intensities $I_{6+}$ and $I_{TL}$, it is possible with a theoretical intensity calculation based on the conventional fundamental parameter method. More simply, the ratio $C_{6+}/C_{TL}$ of the amounts of deposit may be used as the second intensity ratio $I_{6+}/I_{TL}$ as it stands.

Where it is difficult to prepare the standard sample of a kind made up of the chromate treatment film and the substrate in the form of the galvanized sheet steel, a plurality of standard samples of different but known compositions as an alternative may be prepared by mixing a powder of alumina, a powdery reagent of trivalent chrome ($Cr_2O_3$) and a powdery reagent of hexavalent chrome ($CrO_3$ or others) and may be used to determine the first intensity ratio $I_H/I_L$ in a manner similar to that described above and, on the other hand, the ratio of respective concentrations of the hexavalent chrome and the total chrome is used as the second intensity ratio for the determination of the correlation. For example, such a linear correlation as shown in FIG. 2 can be obtained.

Figure 3:
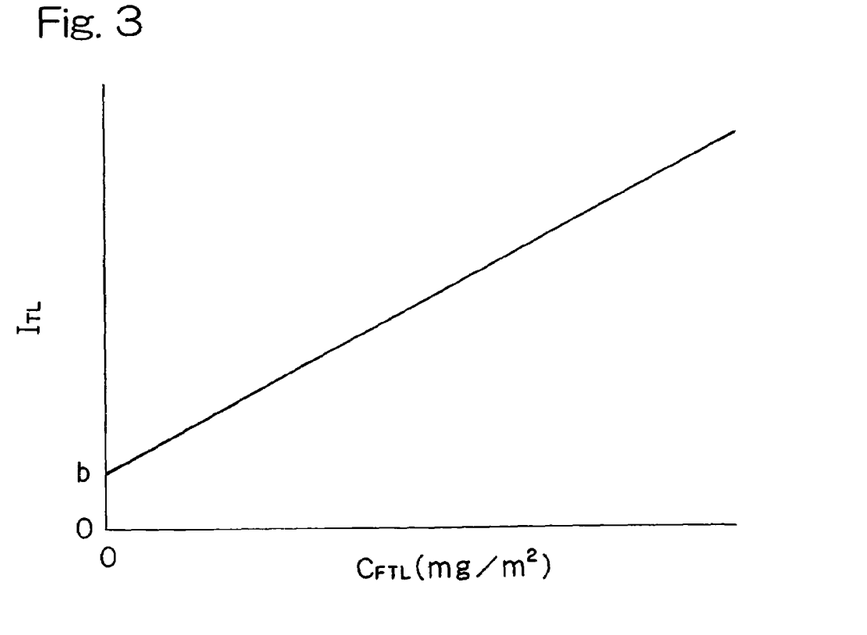
FIG. 3 is a chart showing an example of analytical curve used in the X-ray fluorescence spectrometer.

Also, with respect to the plural standard samples 1A having different but known amounts of deposit in the chromate treatment films 1a and also having the same amount of deposit of metal chrome in the galvanized sheet steels 1b, using the standard detecting device 23A, the intensity $I_{TL}$ of the total chrome at the peak spectroscopic angle is measured and analytical curve descriptive of the relationship between the intensity $I_{TL}$ from the total chrome and the amount of deposit $C_{FTL}$ of the chrome in the chromate treatment film is prepared and stored. By way of example, such linear analytical curve as shown in FIG. 3 can be obtained. The equation of the analytical curve can be expressed as follows.

$$C_{FTL} = AI_{TL} + B$$

$I_{TL} = b = -B/A$, which corresponds to $C_{FTL} = 0$, represents the intensity from metal chrome contained in the galvanized sheet steel 1b and A represents the gradient of the analytical curve. The gradient A of the analytical curve represents a coefficient with which the intensity from the chrome in the chromate treatment film 1a can be converted into the amount of deposit.

Thereafter, by means of the quantitatively analyzing device 18 shown in FIG. 1, with respect to the sample 1B to be analyzed, using the high resolution detecting device 23B the intensity $I_L$ at the predetermined spectroscopic angle $2\theta_L$ on the smaller angle side and the intensity $I_H$ at the predetermined spectroscopic angle $2\theta_H$ on the larger angle side are measured to determine the first intensity ratio $I_H/I_L$, which is then applied to the previously described correlation to secure the second intensity ratio $I_{6+}/I_{TL}$. Also, with respect to the sample 1B to be analyzed, using the standard detecting device 23A, the intensity $I_{TL}$ of the total chrome at the peak spectroscopic angle is measured and the second intensity ratio $I_{6+}/I_{TL}$ is applied to calculate the intensity $I_{6+}$ from the hexavalent chrome. Then, the intensity $I_{6+}$ from the hexavalent chrome is multiplied by the gradient A of the analytical curve to calculate the amount of deposit $C_{6+}$ of the hexavalent chrome contained in the chromate treatment film as $AI_{6+}$. In other words, by the quantitatively analyzing device 18, the amount of deposit $C_{6+}$ of the hexavalent chrome contained in the chromate treatment film with respect to the sample 1B to be analyzed can be automatically calculated.

The X-ray fluorescence spectrometer according to the foregoing embodiment is a so-called single crystal spectrometer as hereinbefore described and, where the sample 1 is made up of a chromate treatment film 1a and a substrate 1b in the form of a sheet steel or a galvanized sheet steel, the quantitatively analyzing device 18 calculates the concentration $C_{6+}$ of the hexavalent chrome based on the fact that the peak spectroscopic angle, at which the maximum intensity is attained in Cr—Kα line 22, varies depending on the ratio $I_{6+}/I_{TL}$ of the intensity of the hexavalent chrome vs. the intensity of the total chrome and, accordingly, the hexavalent chrome can be quantitatively analyzed with a simplified structure and the X-ray fluorescence spectrometer according to the foregoing embodiment can be constructed simply by modifying contents of operation of the quantitatively analyzing device 18 based on the conventional scanning type X-ray fluorescence spectrometer. Also, influences brought about by the metal chrome contained in the substrate $1b$ in the form of the sheet steel or the galvanized sheet steel $1b$ can be excluded. The reason that with such a simple structure the hexavalent chrome can be quantitatively analyzed is because when change of the peak spectroscopic angle is to be detected, that is, when the first intensity ratios $I_H/I_L$ discussed above are to be determined, the detecting device 23B having a higher resolution than that of the detecting device 23A that is selected when the intensities $I_{TL}$ of the total chrome are to be determined is selected.

It is to be noted that in the X-ray fluorescence spectrometer according to the foregoing embodiment, in place of the intensities $I_L$ and $I_H$ at the respective predetermined spectroscopic angles $2\theta_L$ and $2\theta_H$ with respect to the standard sample 1A and the sample 1B to be analyzed, the ratios $I_L/I_{CL}$ and $I_H/I_{CH}$ between the intensities $I_L$ and $I_H$ thereof and the intensities $I_{CL}$ and $I_{CH}$ at the predetermined angles $2\theta_L$ and $2\theta_H$ with respect to monitor sample IC can be used. For the monitor sample 1C, a sample of 100% metal chrome, for example, may be used and is measured with the use of the high resolution detecting device 23B. Although it may occur that due to the use of the spectrometer for a substantial period and/or change in temperature inside the spectrometer, displacement may occur from the predetermined spectroscopic angle, the foregoing construction is effective to correct any influence that is brought about by the displacement of the predetermined spectroscopic angle.

It is, however, to be noted that such correction is effectively used as a correction of a relatively short routine period, such correction will be insufficient in the case of the displacement of the predetermined spectroscopic angle over a substantial period. In view of this, if as a result of the analysis of the monitor sample 1C, which is 100% metal chrome, an analytical error is found to be out of a predetermined range (for example, ±5% or higher), either the standard sample 1A is again measured to form the correlation shown in FIG. 2, or the correlation shown in FIG. 2 is to be modified by the following method.

Specifically, when using the standard sample 1A, the predetermined spectroscopic angle $2\theta_L$ on the smaller angle side and the predetermined angle $2\theta_H$ on the larger angle side are to be determined, with respect to, for example, the monitor sample 1C, which is 100% metal chrome, and the monitor sample IC, which is 100% hexavalent chrome, the intensities $I_L$ and $I_H$ at the predetermined spectroscopic angles $2\theta_L$ and $2\theta_H$ and spectroscopic angles (for example, predetermined spectroscopic angle ±0.01°), which fall within the range of displacement that can be contemplated, are measured and the correlation between the displacement of the predetermined spectroscopic angles and the intensity ratio $I_H/I_L$ is then determined and stored in the quantitatively analyzing device 18. Such linear correlations as shown in FIGS. 5 and 6 can be obtained.

Figure 5:
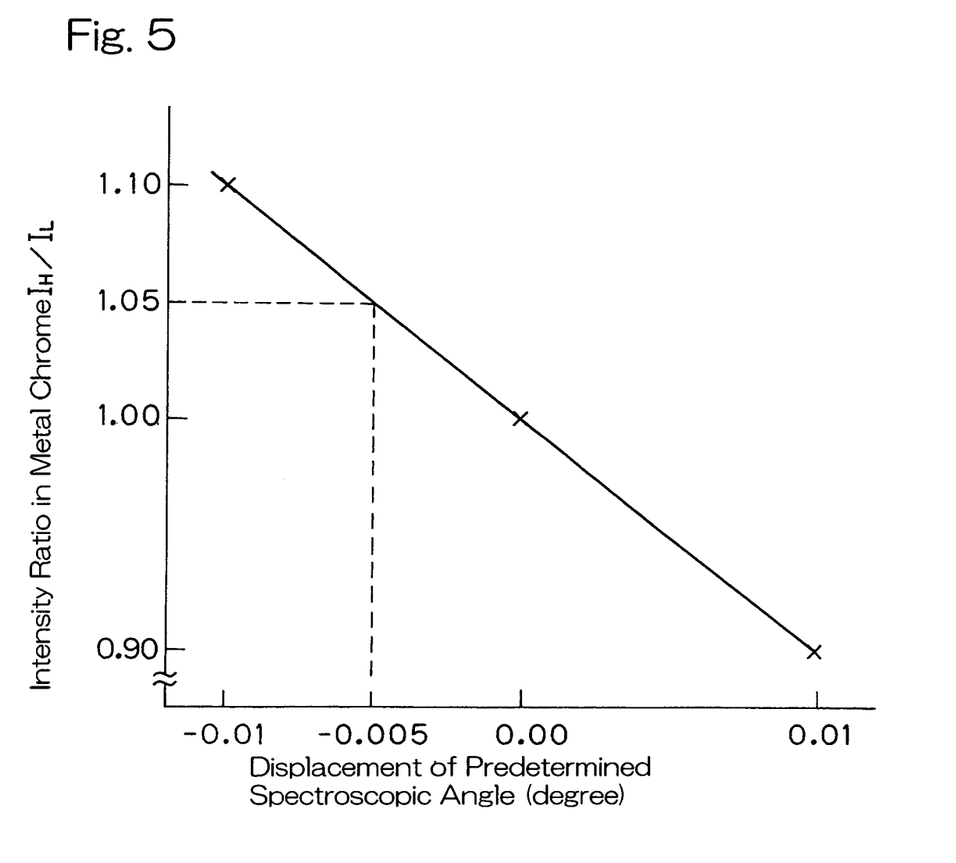
FIG. 5 is a chart showing a correlation that can be used in correcting the analytical curve with the X-ray fluorescence spectrometer shown in FIG. 1.
Figure 6:
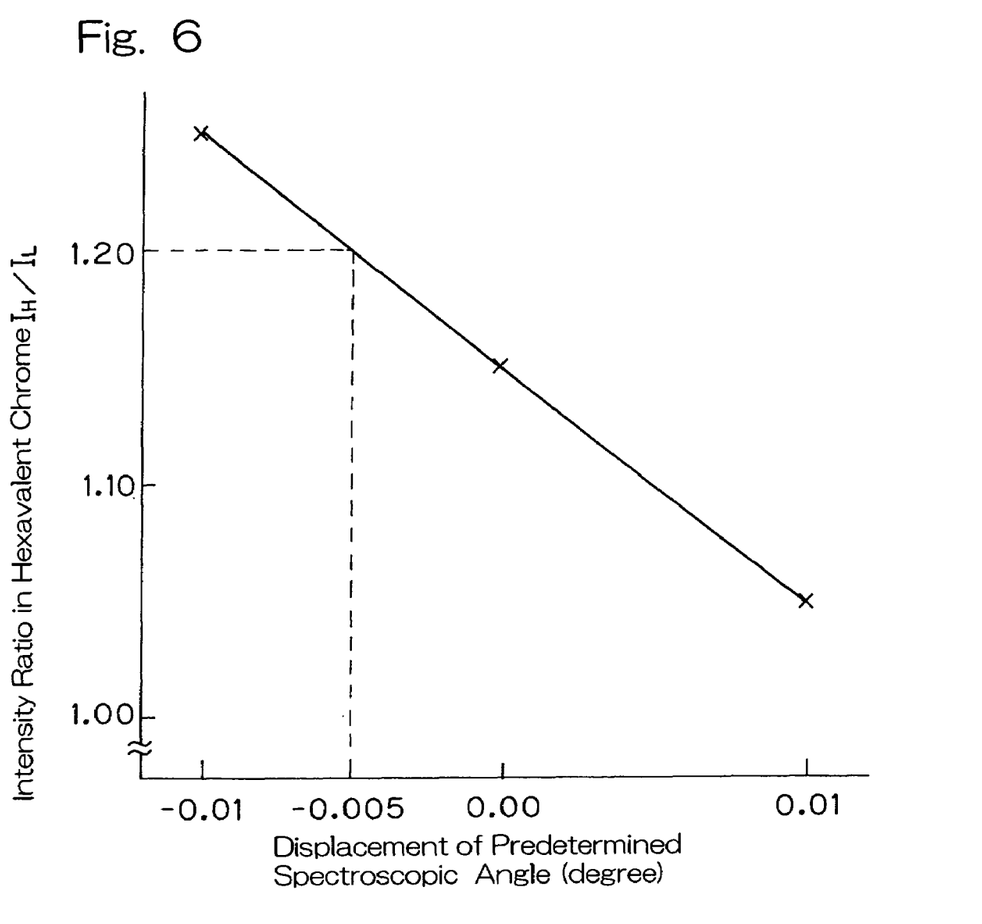
FIG. 6 is a chart showing a different correlation that can be used in correcting the analytical curve with the X-ray fluorescence spectrometer shown in FIG. 1.

When the correlation shown in FIG. 2 is modified in order to correct the influence brought about by the displacement of the predetermined spectroscopic angle, with respect to the monitor sample 1C, which is 100% metal chrome, using the high resolution detecting device 23B in a manner similar to that used when the correlations shown in FIGS. 5 and 6 are prepared, the intensities $I_L$ and $I_H$ are measured while they are set at the predetermined spectroscopic angles $2\theta_L$ and $2\theta_H$ (which are in reality likely to displace), to thereby determine the intensity ratio $I_H/I_L$. If the intensity ratio $I_H/I_L$ is, for example, 1.05, it can readily be ascertained from the correlation shown in FIG. 5 that the displacement of the predetermined spectroscopic angles is −0.005°, that is, that the measurement is actually taking place at the spectroscopic angles $2\theta_L$−0.005° and $2\theta_H$−0.0005°, respectively. Also, when the −0.005° displacement of the predetermined spectroscopic angles are applied to the correlation shown in FIG. 6, 1.20 can be obtained as the intensity ratio $I_H/I_L$ of the hexavalent chrome.

In view of the intensity ratio of the metal chrome being 1.05 and the intensity ratio of the hexavalent chrome being 1.20, the correlation can be modified as shown by the double-dotted line in FIG. 2 and is therefore stored in the quantitatively analyzing device 18. Although there is a method in which each time the correlation of FIG. 2 is modified, the monitor sample 1C, which is 100% hexavalent chrome, too, is measured, the method described above merely requires the measurement of the hexavalent chrome, which has a high toxicity, to be carried out when the correlation shown in FIG. 6 is prepared for the first time.

It is to be noted that in the foregoing description, assumption is made to the quantitative analysis in a narrow sense, in which the quantitatively analyzing device 18 operates to halt the interlocking drive device 10 at the spectroscopic angle at which the measurement is to be carried out. However, where the concentration $W_{TL}$ or the intensity $I_{TL}$ of the total chrome is desired to be determined, a method, i.e., a so-called semi-quantitative analysis, may be carried out, which includes continuously scanning the detector 8 without the interlocking drive device 10 being halted, performing a qualitative analysis based on a result of measurement done by the detector 8, performing a quantitative analysis based on a result of the qualitative analysis and rendering the value of chrome analyzed, appearing in a result of the quantitative analysis, to be the concentration $W_{TL}$ or the intensity $I_{TL}$ of the total chrome.

It is to be noted that since in the X-ray fluorescence spectrometer shown and described in connection with the foregoing embodiment, the divergence slit 11B and the spectroscopic device 6B are common to the standard detecting device 3A and the high resolution detecting device 23B, their replacement is no longer needed, thus bringing about an advantage in terms of reproducibility. In such case, only one may be provided for each of the divergence slit 11 and the spectroscopic device 6 and neither the divergence slit changer 17 nor the spectroscopic device changer 15 may be employed. Other than this, numerous combinations of the divergence slit 11, the spectroscopic device 6, the receiving slit 20 and the detector 8 in each of the standard detecting device 23A and the high resolution detecting device 23B can be contemplated. By way of example, the standard detecting device 23A may be of a structure including a combination of the standard divergence slit 11A, the standard spectroscopic device 6A, the high resolution receiving slit 20B and the detector 8B while the high resolution detecting device 23B may be of a structure including a combination of the high resolution divergence slit 11B, the high resolution spectroscopic device 6B, the high resolution receiving slit 20B and the detector 8B.

According to another aspect of the present invention, the present invention provides a program to be used for enabling a computer, employed in the X-ray fluorescent spectrometer of the structure hereinbefore fully described, to function as the quantitatively analyzing device 18. Even with this program, functions and effects similar to those described in connection with the X-ray fluorescence spectrometer can be obtained.

Although the X-ray fluorescence spectrometer shown and described in connection with the preferred embodiment of the present invention is of a scanning type equipped with the goniometer, an X-ray fluorescence spectrometer of a simultaneous multi-elements analysis type, in which with respect to Cr—Kα line, measurement at the predetermined spectroscopic angles $2\theta_L$ and $2\theta_H$ with a high resolution and measurement at the peak spectroscopic angle with a standard resolution are carried out for each spectroscopic angle by means of a fixed detecting device including a divergence slit, a single spectroscopic device, a receiving slit and a detector, can also be used to quantitatively analyze the hexavalent chrome.

What is claimed is:

1. An X-ray fluorescence spectrometer which comprises:
an X-ray source for irradiating a sample with primary X-rays;
a divergence slit for passing therethrough fluorescent X-rays generated from the sample;
a spectroscopic device for monochromating the fluorescent X-rays having passed through the divergence slit;
a receiving slit for passing therethrough the fluorescent X-rays having been monochromated by the spectroscopic device;
a detector for detecting an intensity of the fluorescent X-rays having passed through the receiving slit;
an interlocking drive device for driving the spectroscopic device, the receiving slit and the detector in association with each other so that while the wavelength of the fluorescent X-rays monochromated at a spectroscopic angle of the spectroscopic device that is changed is varied, the fluorescent X-rays so monochromated can impinge on the receiving slit and the detector; and
a quantitatively analyzing device configured to perform quantitative analysis based on a result of measurement by the detector;
wherein the quantitatively analyzing device calculates the concentration or the amount of deposit of hexavalent chrome based on the fact that the spectroscopic angle of the peak, at which the maximum intensity is attained in the Cr—Kα line, changes depending on a ratio of the concentration or the intensity of the hexavalent chrome vs. the concentration or the intensity of the total chrome; and
wherein at least one of the divergence slit, the spectroscopic device, and the receiving slit is provided selectively in a plural number so as to form a plurality of detecting devices having different resolutions from each other as a combination of the divergence slit, the spectroscopic device, the receiving slit, and the detector, such that when a change of the peak spectroscopic angle is to be detected, a detecting device having a higher resolution than that of the detecting device, which is selected when the concentration or the intensity of the total chrome is to be determined, is selected.

2. The X-ray fluorescence spectrometer as claimed in claim 1, wherein the quantitatively analyzing device stores therein a correlation between a ratio of the intensity at a predetermined spectroscopic angle on a smaller angle side than the peak in the Cr—Kα line vs. the intensity at a predetermined spectroscopic angle on a larger angle side than the peak and a ratio of the concentration of the hexavalent chrome vs. the concentration of the total chrome, which have been determined using a standard sample, and calculates the concentration of the hexavalent chrome in a sample to be analyzed, by determining, with respect to a sample to be analyzed, the ratio of the intensities, applying it to the correlation and applying the concentration of the total chrome so determined to the ratio of the concentrations so obtained, and
wherein the receiving slit is provided selectively in a plural number such that when the ratios of the intensities are to be determined, a receiving slit having a higher resolution than that of a receiving slit, which is selected when the concentrations of the total chrome are determined, is selected.

3. The X-ray fluorescence spectrometer as claimed in claim 1, wherein the sample comprises a chromate treatment film and a substrate in the form of a sheet steel or galvanized sheet steel positioned beneath the chromate treatment film;
wherein the quantitatively analyzing device stores therein a correlation between a ratio of the intensity at a predetermined spectroscopic angle on a smaller angle side than the peak in the Cr—Kα line vs. the intensity at a predetermined spectroscopic angle on a larger angle side than the peak, that is, a first intensity ratio, and a ratio of the intensity from the hexavalent chrome vs. the intensity from the total chrome, that is, a second intensity ratio, which have been determined using a standard sample, and also stores therein an analytical curve descriptive of the relationship between the intensity from the total chrome and the amount of deposit of chrome contained in the chromate treatment film, and calculates the amount of deposit of the hexavalent chrome in the chromate treatment film by, with respect to the sample to be analyzed, determining and applying the first intensity ratio to the correlation, applying the intensity from the total chrome, so determined, to the second intensity ratio to thereby calculate the intensity from the hexavalent chrome and multiplying the intensity from the hexavalent chrome by a gradient of the analytical curve;
wherein the receiving slit is provided selectively in a plural number such that when the first intensity ratios are to be determined, a receiving slit having a higher resolution than that of a receiving slit, which is selected when the intensities from the total chrome are determined, is selected.

4. The X-ray fluorescence spectrometer as claimed in claim 2, wherein in place of the intensity at each of the predetermined spectroscopic angles with respect to the standard sample and the sample to be analyzed, a ratio between the intensity thereof and the intensity at each of the predetermined spectroscopic angles with respect to a monitor sample is utilized.

5. The X-ray fluorescence spectrometer as claimed in claim 3, wherein in place of the intensity at each of the predetermined spectroscopic angles with respect to the standard sample and the sample to be analyzed, a ratio between the intensity thereof and the intensity at each of the predetermined spectroscopic angles with respect to a monitor sample is utilized.

6. The X-ray fluorescence spectrometer as claimed in claim 2, wherein the Cr—Kα1 line is measured using pure metal chrome and trivalent chrome as samples; peak profiles normalized with their integrated intensities are determined; spectroscopic angles, at which respective intensities of the peak profiles forwardly and rearwardly of a peak spectroscopic angle of the Cr—Kα1 line match with each other, is determined; and the quantitatively analyzing device stores therein the two spectroscopic angles, so determined, as the predetermined spectroscopic angle on the smaller angle side and the predetermined spectroscopic angle on the larger angle side, respectively.

7. The X-ray fluorescence spectrometer as claimed in claim 3, wherein the Cr—Kα1 line is measured using pure metal chrome and trivalent chrome as samples; peak profiles normalized with their integrated intensities are determined; spectroscopic angles, at which respective intensities of the peak profiles forwardly and rearwardly of a peak spectroscopic angle of the Cr—Kα1 line match with each other, is determined; and the quantitatively analyzing device stores therein the two spectroscopic angles, so determined, as the predetermined spectroscopic angle on the smaller angle side and the predetermined spectroscopic angle on the larger angle side, respectively.

8. The X-ray fluorescence spectrometer as claimed in claim 1, wherein the quantitatively analyzing device performs, when the concentration or the intensity of the total chrome is to be determined, a qualitative analysis based on a result of measurement done by the detector, performing a quantitative analysis based on a result of the qualitative analysis and rendering the value of chrome analyzed, appearing in a result of the quantitative analysis, to be the concentration or the intensity of the total chrome.

* * * * *